United States Patent
Gravel et al.

(10) Patent No.: US 7,067,488 B2
(45) Date of Patent: Jun. 27, 2006

(54) MODIFIED GLP-1 PEPTIDES WITH INCREASED BIOLOGICAL POTENCY

(75) Inventors: Denis Gravel, St-Lambert (CA); Krishna Peri, St-Laurent (CA); Thierry Abribat, Montréal (CA); Abdelkrim Habi, Dollard des Ormeaux (CA)

(73) Assignee: TheraTechnologies Inc., Saint-Laurent (CA)

( * ) Notice: Subject to any disclaimer, the term of this patent is extended or adjusted under 35 U.S.C. 154(b) by 0 days.

(21) Appl. No.: 10/671,340

(22) Filed: Sep. 25, 2003

(65) Prior Publication Data

US 2004/0127412 A1    Jul. 1, 2004

Related U.S. Application Data

(60) Provisional application No. 60/413,171, filed on Sep. 25, 2002.

(51) Int. Cl.
*A61K 38/22* (2006.01)
*C07K 14/575* (2006.01)

(52) U.S. Cl. ............ 514/12; 514/21; 530/308; 530/324; 530/345

(58) Field of Classification Search ............ 530/308, 530/324, 345; 514/12, 21
See application file for complete search history.

(56) References Cited

U.S. PATENT DOCUMENTS

| | | | |
|---|---|---|---|
| 5,512,549 A | 4/1996 | Chen et al. | 514/12 |
| 5,545,618 A | 8/1996 | Buckley et al. | 514/12 |
| 2004/0018981 A1 * | 1/2004 | Dong | 514/12 |

FOREIGN PATENT DOCUMENTS

| | | |
|---|---|---|
| EP | 0 733 644 | 9/1996 |
| WO | WO 91/11457 | 8/1991 |
| WO | WO 98/08871 | 3/1998 |
| WO | WO 99/43707 | 9/1999 |
| WO | WO 00/55119 | 9/2000 |
| WO | WO 02/10195 | 2/2002 |

OTHER PUBLICATIONS

Adelhorst et al:, "Structure-activity sutides of glucagon-like peptide-1," *J. Biol. Chem.*, 269(9):6275-6278, 1994.
Burcelin et al., "Long-lasting antidiabetic effect of a dipeptidyl peptidase IV-resistant analogy of glucagon-like peptide-1," *Metabolism*, 48(2):252-258, 1999.

(Continued)

*Primary Examiner*—Jeffrey Edwin Russe
(74) *Attorney, Agent, or Firm*—Fulbright & Jaworski

(57) ABSTRACT

The present invention relates to a GLP-1 peptide having the following formula, or a pharmaceutically acceptable salt thereof:

X-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-val-Lys-Gly-Arg-Y (SEQ ID NO. 1)

wherein X is a rigidifying hydrophobic moiety and wherein Y is selected from the group consisting of OH, $NH_2$ and Gly-OH. Moreover, the present invention relates to pharmaceutical compositions comprising a therapeutically effective amount of a peptide of the present invention, or a pharmaceutically acceptable salt thereof, in association with at least one constituent selected from a pharmaceutically acceptable carrier, diluent, and excipient.

23 Claims, 6 Drawing Sheets

OTHER PUBLICATIONS

D'alessio et al., "Glucagon-like peptide 1 decreases hepatic glucose production independent of insulin and glucagon," *Diabetes*, 46(suppl 1):29A, 1997.

Deacon et al., "Dipeptidyl peptidase IV resistant analogues of glucagon-like peptide-1 which have extended metabolic stability and improved biological activity," *Diabetologia*, 41:271-278, 1998.

Doyle and Egan, "Glucagon-like peptide-1," *Recent Prog. Horm. Res.*, 56:377-399, 2001.

Doyle et al., "Insertion of an N-Terminal 6-aminohexanoic acid after the 7 amino acid position of glucagon-like peptide-1 produces a long-acting hypoglycemic agent," *Endocrinology*, 142(10):4462-4468, 2001.

Drucker, "Minireview: the glucagon-like peptides," *Endocrinology*, 142(2):521-527, 2001.

Dugas and Penney, In: *Bioorganic Chemistry*, Springer-Verlag, NY, 54-92, 1981.

Gorrell et al., "CD26: a multifunctional integral membrane and secreted protein of activated lymphocytes," *Scand. J. Immunol.*, 54:249-264, 2001.

Gutniak et al., "Antidiabetogenic effect of glucagon-like peptide-1 (7-36)amide in normal subjects and patients with diabetes mellitus," *The New England Journal of Medicine*, 326:1316-1322, 1992.

Gutniak, "Treatment of diabetes GLP-1: a new kid in town," *International Diabetes Monitor*, 9(2):1-12, 1997.

Holst, "Glucagonlike peptide 1: a newly discovered gastrointestinal hormone," *Gastroenterology*, 107:1848-1855, 1994.

Holst, "Glucagon-like peptide 1 (GLP-1: an intestinal hormone, signaling nutritional abundance, with an unusual therapeutic potential," *Trends Endocrinol. Metab.*, 10(6):229-235, 1999.

Holz et al., "Activation of a cAMP-regulated Ca+2 signaling pathway in pancreatic β-cells by the insulinotropic hormone glucagon-like peptide-1," *J. Biol. Chem.*, 270(30):17749-17757, 1995.

Kieffer and Habener, "The glucagon-like peptides," *Endocrine Reviews*, 20(6):876-913, 1999.

Kreymann et al., "Glucagon-like peptide-1 7-36: a physiological incretin in man," *Lancet*, 2(8571):1300:1304, 1987.

Merrifield, "Solid phase peptide synthesis. I. The synthesis of a tetrapeptide," *Chem. Soc.*, 85:2149-2154, 1962.

Nauck et al., "Reduced incretin effect in Type 2 (non-insulin-dependent) diabetes," *Diabetoligia*, 29:46-52, 1986.

Nauck et al., "Normalization of fasting hyperglycaemia by exogenous glucagon-like peptide 1(7-36 amide) in type 2 (non-insulin-dependent) diabetic patients," *Diabetologia*, 36:741-744, 1993.

Nauck, "Glucagonlike peptide 1," *Curr. Opin. Endocrinol. Diabet.*, 4:291-299, 1997.

Peptide synthesis protocols, Methods in molecular biology, vol. 35, Pennington and Dunn (eds.), Humana Press, 1994.

Perfetti and Merkel, "Glucagon-like peptide-1: a major regulator of pancreatic β-cell function," *European Journal of Endocrinology*, 143:717-725, 2000.

*Remington's Pharmaceutical Sciences*, 15$^{th}$ ed., 33:624-652, Mack Publishing Company, Easton, PA, 1980.

Scrocchi et al., "Glucose intolerance but normal satiety in mice with a null mutation in the glucagon-like peptide 1 receptor gene," *Nature Medicine*, 2(11):1254-1258, 1996.

Siegel et al., "Biological activity of GLP-1-analogues with N-terminal modifications," *Regulatory Peptides*, 79:93-102, 1999.

Stewart and Young, In: *Solid Phase Peptide Synthesis*, 24-66, Freeman, San Francisco, 1969.

Suzuki et al., "Effects of GLP-1 and its fragment peptides on pancreatic hormone release," *Diabetes Res.*, 5(Suppl 1):S30, 1988.

Toft-Nielsen et al., "Continuous subcutaneous infusion of glucagon-like peptide 1 lowers plasma glucose and reduces appetite in type 2 diabetic patients," *Diabetes Care*, 22:1137-1143, 1999.

Tolessa et al., "Inhibitory effect of glucagon-like peptide-1 on small bowl motility," *J. Clin. Invest.*, 102(4):764-774, 1998.

Wang et al., "Glucagon-like peptide-1 can reverse the age-related decline in glucose tolerance in rats," *J. Clin. Invest.*, 99(12):2883-2889, 1997.

Xiao et al., "Biological activities of glucagon-like peptide-1 analogues in vitro and in vivo," *Biochemistry*, 40:2860-2869, 2001.

Xu et al., "Exendin-4 stimulates both β-cell replication and neogenesis, resulting in increased βcell mass and improved glucose tolerance in diabetic rats," *Diabetes*, 48:2270-2276, 1999.

* cited by examiner

SEQUENCE LISTING

<160> NUMBER OF SEQ ID NOS: 1

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

MODIFIED GLP-1 PEPTIDES WITH INCREASED BIOLOGICAL POTENCY

This application claims the benefit of U.S. Provisional Application No. 60/413,171, filed Sep. 25, 2002, of which the entire text is incorporated by reference.

FILED OF THE INVENTION

The present invention relates to modified GLP-1 peptides having increased biological potency.

BACKGROUND OF THE INVENTION

Oral ingestion of food leads to the secretion of insulin and insulin counter regulatory hormones in a concerted effort to control blood glucose levels by increasing glucose and free fatty acid uptake by the liver, muscle and adipose tissue, and to reduce gluconeogenesis from the liver.

Insulin secretion is modulated by secretagogue hormones, termed as incretins, which are produced by enteroendocrine cells. Glucose-dependent insulinotropic peptide (GIP) and glucagon-like peptide-1 (GLP-1) account for almost all of the incretin effect. GIP, but not GLP-1, is ineffective in diabetic subjects. There is thus a great deal of interest in using GLP-1 and its analogues in therapeutic treatments for diabetes [for detailed discussion of GLP-1 physiology, see reviews Kieffer and Habener (1999); Doyle and Egan (2001); Hoist (1999); Perfetti and Merkel (2000); Nauck (1997); Gutniak (1997); Drucker (2001).

A summary of the current knowledge of GLP-1 physiology is provided below. Extensive information and the references to specific aspects are provided in the reviews cited above. GLP-1 is a 30 aa peptide derived from proglucagon, a 160 aa prohormone. Actions of different prohormone convertases in the pancreas and intestine result in the production of glucagons and other ill-defined peptides, whereas cleavage of proglucagon results in the production of GLP-1 and GLP-2 as well as two other peptides. The aa sequence of GLP-1 is 100% homologous in all mammals studied so far, implying a critical physiological role. GLP-1 (7–37) OH is C-terminally truncated and amidated to form GLP-1 (7–36) $NH_2$. The biological effects and metabolic turnover of the free acid GLP-1 (7–37) OH, and the amide, GLP-1 (7–36) NH2, are indistinguishable. By convention, the numbering of the amino acids is based on the processed GLP-1 (1–37) OH from proglucagon. The biologically active GLP-1 is the result of further processing: GLP-1 (7–36) NH2. Thus the first amino acid of GLP-1 (7–37) OH or GLP-1 (7–36)NH2 is His7.

In the gastrointestinal tract, GLP-1 is produced by L-cells of intestinal, colonic and rectal mucosa, in response to stimulation by intraluminal glucose. The plasma half-life of active GLP-1 is <5 minutes, and its metabolic clearance rate is around 12–13 minutes (Holst, 1994). The major protease involved in the metabolism of GLP-1 is dipeptidyl peptidase (DPP) IV (CD26) which cleaves the N-terminal His-Ala dipeptide, thus producing metabolites, GLP-1 (9–37) OH or GLP-1 (9–36) $NH_2$ which are variously described as inactive, weak agonist or antagonists of GLP-1 receptor. GLP-1 receptor (GLP-1R) is a G protein coupled receptor of 463 aa and is localized in pancreatic beta cells, in the lungs and to a lesser extent in the brain, adipose tissue and kidneys. The stimulation of GLP-1R by GLP-1 (7–37) OH or GLP-1 (7–36)$NH_2$ results in adenylate cyclase activation, cAMP synthesis, membrane depolarization, rise in intracellular calcium and increase in glucose-induced insulin secretion (Holz et al., 1995).

GLP-1 is the most potent insulin secretagogue that is secreted from the intestinal mucosa in response to food intake. Fasting levels of immunoreactive GLP-1 in humans is about 5–10 pmol/L and rises to 25 pmol/L post-prandially (Perfetti and Merkel, 2000 vide supra). The profound incretin effect of GLP-1 is underscored by the fact that GLP-1R knockout mice are glucose-intolerant (Scrocchi et al.,). The incretin response of iv infused GLP-1 is preserved in diabetic subjects, though the incretin response to oral glucose in these patients is compro mised. GLP-1 administration by infusion or sc injections controls fasting glucose levels in diabetic patients, and maintains the glucose threshold for insulin secretion (Gutniak et al. 1992; Nauck et al., 1986; Nauck et al., 1993). GLP-1 has shown tremendous potential as a therapeutic agent capable of augmenting insulin secretion in a physiological manner, while avoiding hypoglycemia associated with sulfonylurea drugs.

Other important effects of GLP-1 on glucose homeostasis are suppression of glucagon secretion and inhibition of gastric motility (Tolessa et al., 1998). GLP-1 inhibitory actions on alpha cells of the pancreas leads to decreases in hepatic glucose production via reduction in gluconeogenesis and glycogenolysis (D'Alessio et al., 1997). This antiglucagon effect of GLP-1 is preserved in diabetic patients.

The so-called ileal brake effect of GLP-1, in which gastric motility and gastric secretion are inhibited, is effected via vagal efferent receptors or by direct action on intestinal smooth muscle. Reduction of gastric acid secretion by GLP-1 contributes to a lag phase in nutrient availability, thus obviating the need for rapid insulin response. In summary, the gastrointestinal effects of GLP-1 contribute significantly to delayed glucose and fatty acid absorption and modulate insulin secretion and glucose homeostasis.

GLP-1 has also been shown to induce beta cell specific genes, such as GLUT-1 transporter, insulin receptor (via the interaction of PDX-1 with insulin promoter), and hexokinase-1. Thus GLP-1 could potentially reverse glucose intolerance normally associated with aging, as demonstrated by rodent experiments (Perfetti and Merkel. 2000. vide supra). In addition, GLP-1 may contribute to beta cell neogenesis and increase beta cell mass, in addition to restoring beta cell function (Wang et al., 1997; Xu et al., 1999).

Central effects of GLP-1 include increases in satiety coupled with decreases in food intake, effected via the action of hypothalamic GLP-1R. A 48 hour continuous sc infusion of GLP-1 in type II diabetic subjects, decreased hunger and food intake and increased satiety (Toft-Nielsen et al., 1999). These anorectic effects were absent in GLP-1R knock out mice (Scrocchi et al., 1996 vide supra).

In summary, the diverse roles played by GLP-1 in maintaining metabolic homeostasis, makes it an ideal drug candidate for treating diabetes, obesity and metabolic syndrome.

Stability of GLP-1 in Circulation

GLP-1 released from the L-cells of the intestine, in response to food, enters portal circulation. It is rapidly cleaved by DPP IV (CD26) to release GLP-1 (9–37) or GLP-1 (9–36) amide, both of which are less active at GLP-1R. According to some reports, they may act as antagonists of GLP-1R and GLP-1 effects on gastrointestinal motility. The half-life of circulating GLP-1 was found to be about 4 minutes (Kreymann et al., 1987). Dipeptidyl-peptidase IV (DPP IV, EC 3.4.14.5, CD26), designated CD26, is an extracellular membrane-bound enzyme, expressed on the surface of several cell types, in particular $CD4^+$ T-cells, as well as on kidney, placenta, blood plasma, liver, and intestinal cells. On T-cells, DPP IV has been shown to be identical to the antigen CD26. CD26 is expressed on a fraction of resting T cells at low density, but is strongly up-regulated following T-cell activation (Gorrell et al., 2001). Recent results indicate that CD26 is a multifunctional molecule that may have an important functional role in T-cells and in overall immune system modulation. CD26 is associated with other receptors of immunological significance found on the cell surface, such as the protein tyrosine phosphatase CD45 and adenosine deaminase (ADA). DPP IV exerts a negative regulation of glucose disposal by degrading GLP-1 and GIP, thus lowering the incretin effect on beta cells of the pancreas.

DPP IV-resistant Analogues of GLP-1

DPP IV cleaves the Ala-Asp bond of the major circulating form of human GLP-1 (human GLP-1 (7–36) NH2: His-Ala-Glu-Gly-Thr-Phe-Thr-Ser-Asp-Val-Ser-Ser-Tyr-Leu-Glu-Gly-Gln -Ala-Ala-Lys-Glu-Phe-Ile-Ala-Trp-Leu-Val-Lys-Gly-Arg-NH2) (SEQ ID NO:1), releasing an N-terminal dipeptide.

Substitution of Ala with Gly (Deacon et al., 1998; Burcelin et al., 1999), Leu, D-Ala and other amino acids, was shown to protect GLP-1 from DPP IV degradation and potentiates its in-vitro and in-vivo insulinotropic actions (Xiao et al., 2001).

Deletion of the amino-terminal histidine, or of the NH2 group of His7, decreased receptor affinity and potency of the analogue (Adelhorst et al., 1994; Xiao et al. 2001 vide supra; Siegel et al., 1999).

U.S. Pat. No. 5,545,618 teaches that N-terminal modifications using alkyl and acyl modifications also produced DPP IV resistant analogues. More specifically, His7 substitution by N-alkylated ($C_{1-6}$) or N-acylated ($C_{1-6}$) L-/D-amino acids resulted in analogues possessing DPP IV-resistance. However, the examples given in this patent only cover acetyl and isopropyl groups.

Covalent coupling of unsaturated organic acids, such as trans-3-hexenoic acid, also produces DPP IV-resistant GLP-1 analogs that potently reduce hyperglycemia in oral glucose tolerance tests in mice (Xiao et al. 2001 vide supra). Furthermore, His7 can be replaced by α-substituted carboxylic acids, one of the substituents being a 5- or 6-membered ring structure (e.g. imidazole), in order to confer DPP IV resistance (WO 99/43707). Insertion of 6-aminohexanoic acid (AHA) after His7 was shown to confer DPP IV resistance, while retaining receptor affinity and insulinotropic efficacy in vivo (Doyle et al., 2001).

Numerous GLP-1 analogs demonstrating insulinotropic action are known in the art. These variants and analogs include, for example, GLP-1(7–36), Gln9-GLP-1(7–37), D-Gln9-GLP-1(7–37), acetyl-Lys9-GLP-1(7–37), Thr16-Lys18-GLP-1(7–37), and Lys18-GLP-1(7–37). Derivatives of GLP-1 include, for example, acid addition salts, carboxylate salts, lower alkyl esters, and amides (WO 91/11457 (1991); EP 0 733,644 (1996); and U.S. Pat. No. 5,512,549 (1996)). It has also been demonstrated that the N-terminal histidine residue (His7) is very important to the insulinotropic activity of GLP-1 (Suzuki et al., 1988).

Modification of His7 by alkyl or acyl (C1–6) groups, and replacement of His with functionally-equivalent C5–6 ring structures appears to confer DPP IV resistance. However, current information does not divulge if all covalent modifications of His7 also retain GLP-1 function in vitro and in vivo.

There thus remains a need to develop modified GLP-1 peptides having increased biological potency.

The present invention seeks to meet these and other needs.

The present description refers to a number of documents, the content of which is herein incorporated by reference in their entirety.

SUMMARY OF THE INVENTION

The present invention relates to a GLP-1 peptide having the following formula, or a pharmaceutically acceptable salt thereof:

X-His-Ala-Glu-Gly-Thr-Phe-Thr-Ser-Asp-Val-Ser-
Ser-Tyr-Leu-Glu-Gly-Gln-Ala-Ala-Lys-Glu-Phe-
Ile-Ala-Trp-Leu-val-Lys-Gly-Arg-Y (SEQ ID
NO. 1)

wherein X is a rigidifying hydrophobic moiety selected from the group consisting of:

i. $C_1$–$C_{10}$ alkenoic acid, with the proviso that the alkenoic acid is not trans-3-hexenoic acid; wherein the alkenoic acid can be substituted by at least one substituent selected from the group consisting of straight or branched $C_1$–$C_6$ alkyl, $C_3$–$C_6$ cycloalkyl, aryl and substituted aryl;

ii. $C_1$–$C_{10}$ alkynoic acid;

iii. $C_3$–$C_{10}$ cycloalkanoic acid or heterocycloalkanoic acid; wherein the heterocycloalkanoic acid includes a heteroatom selected from the group consisting of O, S and N;

iV. $C_5$–$C_{14}$ arylcarboxylic or arylalkanoic acid, wherein the arylcarboxylic or arylalkanoic acid can be substituted by at least one substituent selected from the group consisting of lower alkyl, lower alkoxy, lower alkylthio, halo, hydroxy, trifluoromethyl, amino, —NH(lower alkyl), —N(lower alkyl)$_2$, di- and tri-substituted phenyl, 1-naphthyl, and 2-naphthyl; wherein the di- and tri-substituted phenyl, 1-naphthyl, and 2-naphthyl are substituted with a substituent selected from the group consisting of methyl, methoxy, methylthio, halo, hydroxy, and amino;

v. C5–C14 heteroarylcarboxylic or heteroarylalkanoic acid, wherein the heteroarylcarboxylic or heteroarylalkanoic acid includes a heteroatom selected from the group consisting of O, S and N, and wherein the heteroarylcarboxylic or heteroarylalkanoic group can be substituted by at least one substituent selected from the group consisting of lower alkyl, lower alkoxy, lower alkylthio, halo, hydroxy, trifluoromethyl, amino, —NH(lower alkyl), or —N(lower alkyl)$_2$, di- and tri-substituted phenyl, 1-naphthyl, and 2-naphthyl; wherein the di- and tri-substituted phenyl, 1-naphthyl, and 2-naphthyl are substituted with a substituent selected from the group consisting of methyl, methoxy, methylthio, halo, hydroxy, and amino; and Y is selected from the group consisting of OH, NH2 and Gly-OH.

In one particular embodiment, the present invention relates to a peptide wherein X is selected from the group consisting of In a second particular embodiment, the present invention relates to a peptide wherein X is selected from the group consisting of 3-aminophenyl acetyl, 3-methoxyphenyl acetyl, salicyl, (1R, 2R) 2-ethylcyclopropyl acetyl, and (1S, 2S) 2-ethylcyclopropyl acetyl.

The present invention relates to a composition comprising a therapeutically effective amount of a peptide of the present invention, or a pharmaceutically acceptable salt thereof, in association with at least one constituent selected from the group consisting of pharmaceutically acceptable carrier, diluent and excipient.

In a particular embodiment, the present invention relates to a composition, wherein the therapeutically effective amount is comprised between about 1 mcg and about 10 mg.

The present invention relates to a composition comprising a prophylactically effective amount of a peptide of the present invention, or a pharmaceutically acceptable salt thereof, in association with at least one constituent selected from the group consisting of pharmaceutically acceptable carrier, diluent and excipient.

The present invention further relates to a method of treating a disease or condition associated with a disorder of glucose metabolism. The invention, in yet another embodiment relates to a prevention (e.q. prophylaxis) of a disease or condition associated with glucose metabolism. Non-limiting examples of glucose disorder include: diabetes mellitus of Type I or Type II, or insulin resistance, weight disorders and diseases or conditions associated thereto, wherein such weight disorders or associated conditions include obesity, overweight-associated conditions, satiety deregulation, reduced plasma insulin levels, increased blood glucose levels, or reduced pancreatic beta cell mass.

In one embodiment, the present invention relates to a method for treating diabetes mellitus of Type I or Type II, comprising the step of administering to a subject in need of such treatment a therapeutically effective amount of the peptide of the present invention, or a pharmaceutically acceptable salt thereof.

In a second embodiment, the present invention relates to a method for treating insulin resistance, comprising the step of administering to a subject in need of such treatment a therapeutically effective amount of the peptide of the present invention, or a pharmaceutically acceptable salt thereof.

In a third embodiment, the present invention relates to a method for weight lowering of a subject, comprising the step of administering an effective amount of the peptide of the present invention, or a pharmaceutically acceptable salt thereof, to the subject.

In a fourth embodiment, the present invention relates to a method for reducing satiety of a subject, comprising the step of administering a therapeutically effective amount of the peptide of the present invention, or a pharmaceutically acceptable salt thereof to the subject in need thereof.

In a fifth embodiment, the present invention relates to a method for post-prandially increasing plasma insulin levels in a subject, comprising the step of administering a therapeutically effective amount of the peptide of the present invention, or a pharmaceutically acceptable salt thereof, to the subject.

In a sixth embodiment, the present invention relates to a method for reducing fasting blood glucose levels in a subject, comprising the step of administering a therapeutically effective amount of the peptide of the present invention, or a pharmaceutically acceptable salt thereof, to the subject.

In a seventy embodiment, the present invention relates to a method for increasing pancreatic beta cell mass in a subject, comprising the step of administering a therapeutically effective amount of the peptide of the present invention, or a pharmaceutically acceptable salt thereof to the subject.

In a particular embodiment, the present invention relates to a method, wherein the peptide, or a pharmaceutically acceptable salt thereof, is administered to a subject through an administration route selected from the group consisting of subcutaneous, intravenous, transdermal, oral, bucal, and intranasal.

In a particular embodiment, the present invention relates to a method, wherein the subject is a human.

The present invention further relates to a use of the peptide of the present invention, or a pharmaceutically acceptable salt thereof, for treating diabetes mellitus of Type I or Type II in a subject.

The present invention further relates to a use of the peptide of the present invention, or a pharmaceutically acceptable salt thereof, for treating insulin resistance in a subject.

The present invention further relates to a use of the peptide of the present invention, or a pharmaceutically acceptable salt thereof, for lowering weight of a subject.

The present invention further relates to the use of the peptide of the present invention, or a pharmaceutically acceptable salt thereof, for reducing satiety of a subject.

The present invention further relates to the use of the peptide of the present invention, or a pharmaceutically acceptable salt thereof, for post-prandially increasing plasma insulin levels in a subject.

The present invention further relates to the use of the peptide of the present invention, or a pharmaceutically acceptable salt thereof, for reducing fasting blood glucose level in a subject.

The present invention further relates to the use of the peptide of the present invention, or a pharmaceutically acceptable salt thereof, for increasing pancreatic beta cell mass in a subject.

The present invention further relates to the use of the peptide of the present invention, or a pharmaceutically acceptable salt thereof, for the preparation of a medicament for treating diabetes mellitus of Type I or Type II in a subject.

The present invention further relates to the use of the peptide of the present invention, or a pharmaceutically acceptable salt thereof, for the preparation of a medicament for treating insulin resistance in a subject.

The present invention further relates to the use of the peptide of the present invention, or a pharmaceutically acceptable salt thereof, for the preparation of a medicament for lowering weight of a subject.

The present invention further relates to the use of the peptide of the present invention, or a pharmaceutically acceptable salt thereof, for the preparation of a medicament for increasing satiety of a subject.

The present invention further relates to the use of the peptide of the present invention, or a pharmaceutically acceptable salt thereof, for the preparation of a medicament for post-prandially increasing plasma insulin levels in a subject.

The present invention further relates to the use of the peptide of the present invention, or a pharmaceutically acceptable salt thereof, for the preparation of a medicament for reducing fasting blood glucose levels in a subject.

Finally, the present invention relates to the use of the peptide of the present invention, or a pharmaceutically acceptable salt thereof, for the preparation of a medicament for increasing pancreatic beta cell mass in a subject.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying drawings, showing by way of illustration a preferred embodiment thereof, and in which.

Other objects, advantages and features of the present invention will become more apparent upon reading of the following non-restrictive description of preferred embodiments with reference to the accompanying drawing(s), which is exemplary and should not be interpreted as limiting the scope of the present invention.

DETAILED DESCRIPTION OF THE INVENTION

Definitions:

As used herein, the term "subject" is intended to mean a mammal selected from the group consisting of human, porcine, bovine, caprine, ovine, feline, canine and equine.

As used herein, the term "GLP-1 analogues" is intended to mean analogues which are biologically-active GLP-1 peptides that include GLP-1 (7–37)OH, GLP-1 (7–36)NH$_2$ and their derivatives; these derivatives include peptides that contain amino acid substitutions, made with the intention of improving solubility (replacement of hydrophobic amino acids with hydrophilic amino acids, PEGylation of terminal carboxyl groups or the ε-amino group of lysine), conferring resistance to oxidation (substitution of Met, Trp, Gln, Asn), increasing biological potency in in vitro and in vivo assays (one or more amino acid substitutions at positions 11, 12, 16, 22, 23, 24, 25, 27, 30, 33, 34, 35, 36, or 37, but not those at 8), or increasing half-life in circulation (acyl ($C_{12}$–$C_{18}$) modifications of the ε-amino group of lysine).

As used herein, the term "rigidifying hydrophobic moiety" is intended to mean a conformationally rigid moiety, which has a limited number of spatial orientations due to the presence of one or more rigidifying elements in its backbone such as, a double bond, a triple bond, or a saturated or unsaturated ring, which have little or no conformational mobility. As a result, the number of conformers or rotational isomers is reduced when compared to the corresponding straight, or unsubstituted and saturated aliphatic chain. These rigidifying hydrophobic moieties are divided into the following groups:

Group 1: Straight or branched alkenoic acid derivatives, e.g.:

Group 2: Straight or branched alkynoic acid derivatives, e.g.:

Group 3: Cycloalkanoic or heterocycloalkanoic acid derivatives, e.g.:

(1S,2S)  cis(+,-) racemic

(1R,2R)

Group 4: Aryl, arylalkanoic, heteroaryl or heteroarylalkanoic acid derivatives, e.g.:

OMe

As used herein, the term "unit dosage form" refers to physically discrete units, suitable as unitary dosages for human subjects and other mammals; each unit containing a predetermined quantity of active material calculated to produce the desired therapeutic effect, in association with one/or more suitable pharmaceutical excipients.

As used herein, the term "aryl" refers to phenyl, 1-naphthyl, and 2-naphthyl.

As used herein, the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), —N(lower alkyl)$_2$, as well as di- and tri-substituted phenyl, 1-naphthyl, or 2-naphthyl, the di- and tri-substituted phenyl, 1-naphthyl, and 2-naphthyl comprising a substituent selected from the group consisting of methyl, methoxy, methylthio, halo, hydroxy, and amino.

The present invention also includes salt forms of GLP-1 analogs. A GLP-1 analog of the present invention may be sufficiently acidic or sufficiently basic to react with any of a number of organic and inorganic bases, and organic and inorganic acids, to form a salt. Acids commonly employed to form acid addition salts are inorganic acids such as hydrochloric acid, hydrobromic acid, hydroibdic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid. A more preferred acid addition salt is formed with hydrochloric acid.

Base addition salts include those derived from inorganic bases, such as ammonium or alkali or alkaline earth metal hydroxides, carbonates, bicarbonates, and the like. Such bases, useful in preparing the salts of this invention, thus include sodium hydroxide, potassium hydroxide, ammonium hydroxide, potassium carbonate, and the like. Salt forms of GLP-1 analogs are particularly preferred. Of course, when the compounds of the present invention are used for therapeutic purposes, the compounds may also be in the form of a salt, however, the salt must be a pharmaceutically acceptable salt.

The present invention relates to a GLP-1 peptide, modified by the covalent attachment of a hydrophobic group to the N-terminus, thus resulting in protease resistance, more specifically DPP IV resistance.

Given the sequence information as disclosed herein, and the state of the art in solid phase protein synthesis, GLP-1 analogs can be obtained via chemical synthesis. The principles of solid phase chemical synthesis of polypeptides are well known in the art (Dugas and Penney, 1981; Merrifield, 1962; Stewart and Young, 1969).

Examples for synthesizing the peptides of the present invention are provided below.

The present invention also relates to pharmaceutical compositions comprising a GLP-1 analog of the present invention, in combination with a pharmaceutically acceptable carrier, diluent, or excipient. Such pharmaceutical compositions are prepared in a manner well known in the pharmaceutical art, and are administered individually or in combination with other therapeutic agents, preferably via parenteral routes. Especially preferred routes of administration include intramuscular and subcutaneous administration.

Parenteral daily dosages, preferably a single daily dose, are typically in the range of from about 1 mcg/kg to about 100 mcg/kg of body weight, although lower or higher dosages may be administered. The required dosage will depend upon the severity of the condition of the patient and upon such criteria as the patient's height, weight, sex, age, and medical history.

In making the compositions of the present invention, the active ingredient, which comprises at least one peptide of the present invention, is usually mixed or diluted with an excipient. When an excipient is used as a diluent, it may be a solid, semi-solid, or liquid material which acts as a vehicle, carrier, or medium for the active ingredient.

Examples of suitable excipients include, but are not limited to lactose, dextrose, sucrose, trehalose, sorbitol, mannitol, starches, gum acacia, calcium silicate, microcrystalline cellulose, polyvinylpyrrolidone, cellulose, water, syrup, and methyl cellulose. The formulations can additionally include lubricating agents such, but not limited to, talc, magnesium stearate and mineral oil. The formulations may further include wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient following administration to the patient, by employing formulation procedures well known in the art.

The compositions of the present invention are preferably formulated in unit dosage form, with each dosage normally containing from about 1 mcg to about 10 mg of the active ingredient.

Additional pharmaceutical methods may be employed to control the duration of action. Controlled release preparations may be achieved by the use of polymers to complex or absorb a peptide of the present invention. The controlled delivery of the active ingredient (peptide) may be exercised by selecting appropriate macromolecules (for example, polyesters, polyamino acids, polyvinylpyrrolidone, ethylene vinylacetate copolymers, methylcellulose, carboxymethylcellulose, and protamine sulfate), the concentration of the macromolecules as well as the methods of incorporation. Such teachings are disclosed in Remington's Pharmaceutical Sciences (1980).

Another possible method to control the duration of action by controlled release preparations, is to incorporate a peptide of the present invention into particles of a polymeric material such as polyesters, polyamino acids, hydrogels, poly (lactic acid) or ethylene vinylacetate copolymers.

The present invention is illustrated in further detail by the following non-limiting examples.

EXAMPLE 1

Solid Phase Synthesis of GLP-1 (7–37)COOH or GLP-1 (7–37)CONH$_2$ and Coupling of Rigid Hydrophobic Pharmacophores The analogues of the present invention are made by solid phase peptide synthesis, using fluorenylmethoxycarbonyl-protected L-amino acids (Peptide synthesis protocols, 1994). Completion of coupling was monitored by the Kaiser color test. The organic acids disclosed in Table 1 were coupled by the same method as used for coupling amino acids. The crude peptides were further purified by preparative HPLC on Vydac C$_{18}$-columns using an acetonitrile gradient in 0.1% TFA. The peptides were vacuum-dried to remove acetonitrile, and lyophilized from 0.1% TFA. Purity was assessed by analytical HPLC and masses were determined by MALDI-TOF mass spectroscopy using a Voyager Biospectrometry Workstation (Perspective Systems). The peptides were prepared as TFA salts and dissolved in saline for administration to animals.

TABLE 1

R represents HN-[His7] GLP-1 (7–37)COOH OR HN-[His7] GLP-1 (7–36)CONH$_2$.

EXAMPLE 2

Effects of GLP-1, 5, 8, 16 and 17 on cAMP Production in RINm5F Cells

RINm5F cells (ATCC # CRL-2058) were grown to confluence and used 4 days following confluency. Aqueous stock solutions (1 mM) of GLP-1, 5, 8, 16, and 17, also containing 0.1% BSA, were made prior to the assay. The numbers refer to compounds listed in Table 2. Cells were pre-incubated with 100 µl RPMI containing 0.5 mM IBMX for 10 minutes at 37° C. Diluted ($10^{-5}$ to $10^{-11}$ M) peptides (100 µl) were added to the wells and incubated for 40 minutes. At the end of the incubation period, the supernatant was collected and assayed for cAMP using a radioimmunoassay kit (Diagnostic Product Corporation). Maximal responses (pmol/mg protein) and IC$_{50}$ (nM) values were evaluated from the dose-response curves and data presented in Table 3.

TABLE 2

GLP-1 analogues containing rigid hydrophobic pharmacophores.

| Compound | Description of GLP-1 peptide |
|---|---|
| Wild type | GLP-1 (7–37) OH |
| 1 | [H7] diphenylacetic acid GLP-1 (7–37) COOH |
| 2 | [H7] O-tolylacetic acid GLP-1 (7–37) COOH |
| 3 | [H7] α-phenyl O-toluic acid GLP-1 (7–37) COOH |
| 4 | [H7] (+, −) cis 2-ethylcyclopropyl acetic acid GLP-1 (7–37) COOH |
| 5 | [H7] 3-aminophenyl acetic acid GLP-1 (7–37) COOH |
| 6 | [H7] 2-ethoxybenzoic acid GLP-1 (7–37) COOH |
| 7 | [H7] 3-methoxyphenyl acetic acid GLP-1 (7–37) COOH |
| 8 | [H7] Salicylic acid GLP-1 (7–37) COOH |
| 9 | [H7] n-phenyl anthranilic acid GLP-1 (7–37) COOH |
| 10 | [H7] 3-(phenylthio)acrylic acid GLP-1 (7–37) COOH |
| 11 | [H7] 2,6-difluorophenyl acetic acid GLP-1 (7–37) COOH |
| 12 | [H7] 2,3,4,5,6-pentafluorophenyl acetic acid GLP-1 (7–37) COOH |
| 13 | [H7] 3-hydroxy phenyl acetic acid GLP-1 (7–37) COOH |
| 14 | [H7] (1R, 2R) 2-ethylcyclopropyl acetic acid GLP-1 (7–37) COOH |
| 15 | [H7] (1S, 2S) 2-ethylcyclopropyl acetic acid GLP-1 (7–37) COOH |
| 16 | [H7] 3-aminophenyl acetic acid GLP-1 (7–36) $CONH_2$ |
| 17 | [H7] Salicylic acid GLP-1 (7–37) $CONH_2$ |

TABLE 3

Effects of GLP-1, 5, 8, 16 and 17 on cAMP production in RINm5F cells.

| Agent | $IC_{50}$ (nM) | Maximal Response (pmol/mg protein) | n |
|---|---|---|---|
| GLP-1 | 6.4 ± 3.8 | 17.6 ± 5.1 | 10 |
| 5 | 8.7 ± 9.8 | 20.0 ± 6.9 | 4 |
| 8 | 13.9 ± 15.6 | 25.1 ± 11.9 | 5 |
| 16 | 10.2 ± 7.7 | 13.8 ± 3.6 | 5 |
| 17 | 13.2 ± 5.2 | 21.9 ± 2.1 | 6 |

Mean ± SD;
n = number of experiments done in duplicate.

EXAMPLE 3

Figure 1:
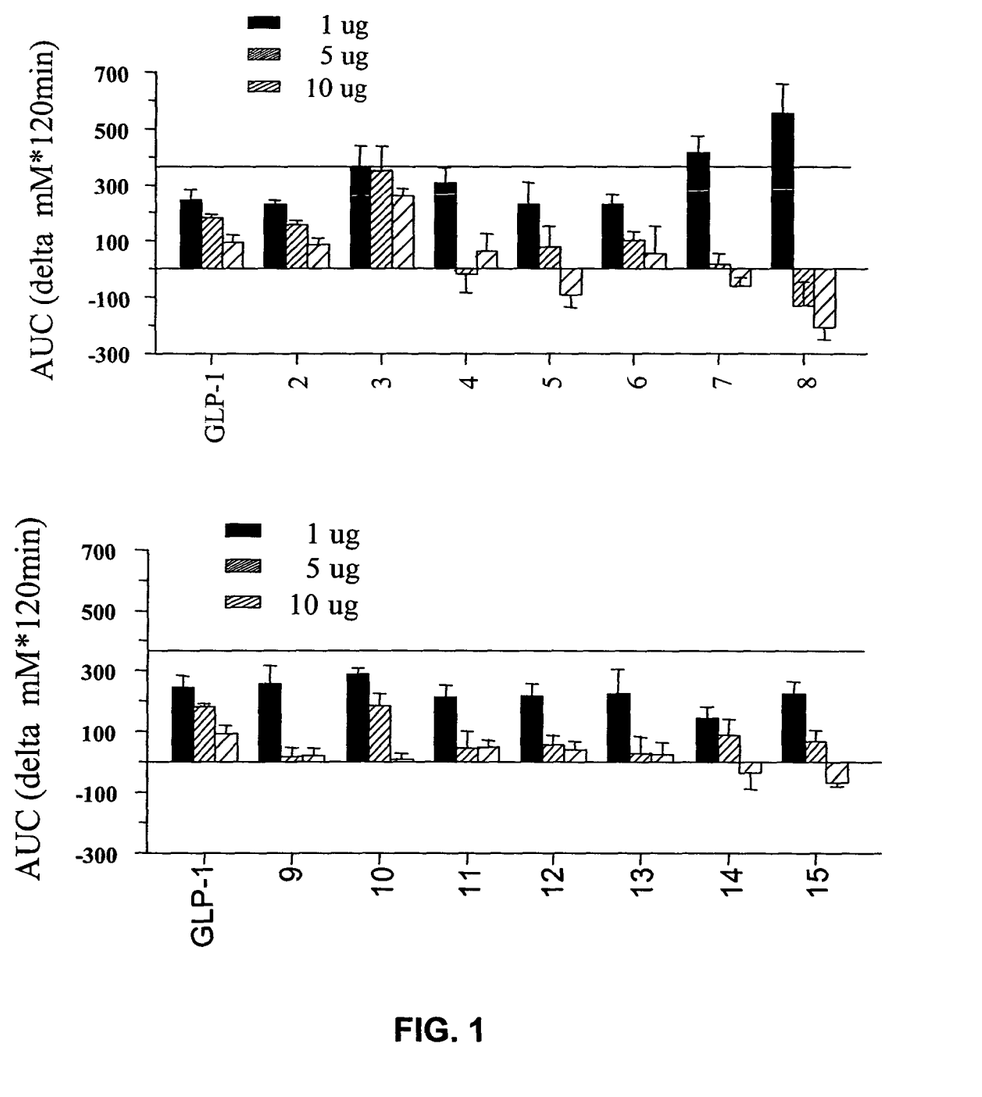
FIG. 1 illustrates glucose disposal produced by GLP-1 analogues using the Oral glucose tolerance test (OGTT), in CD-1 normal female mice (6 wk. Charles River, Montreal, Canada)

Testing the Biological Activity of GLP-1 Analogues Using the Oral Glucose Tolerance Test GLP-1 peptides (1, 5 and 10 μg per mouse) were injected i.p. into overnight fasted CD-1 normal female mice (6 wk. Charles River, Montreal, Canada) 5 minutes prior to an oral glucose challenge (40% glucose solution); glucose (1 g/kg body weight) was administered by oral gavage at t=0 minutes, and blood samples were drawn by tail vein excision; blood glucose levels (mmol/L) were determined at t=0, 10, 20, 30, 60, 90 and 120 minutes using a One-Touch glucometer (Lifescan Canada, Burnaby, BC, Canada). The area under the curve (AUC Glucose [mmol/L*120 min]) was calculated using the trapezoidal method (N=3–4 animals per group). The results are shown in FIG. 1. The horizontal line represents vehicle control (n=50). There was a dose dependent improvement in glucose clearance in all cases. At the highest dose tested, compounds 5, 7, 8, 14, and 15 were clearly superior in efficacy to an identical same dose of GLP-1 (7–37)COOH.

EXAMPLE 4

Figure 2:
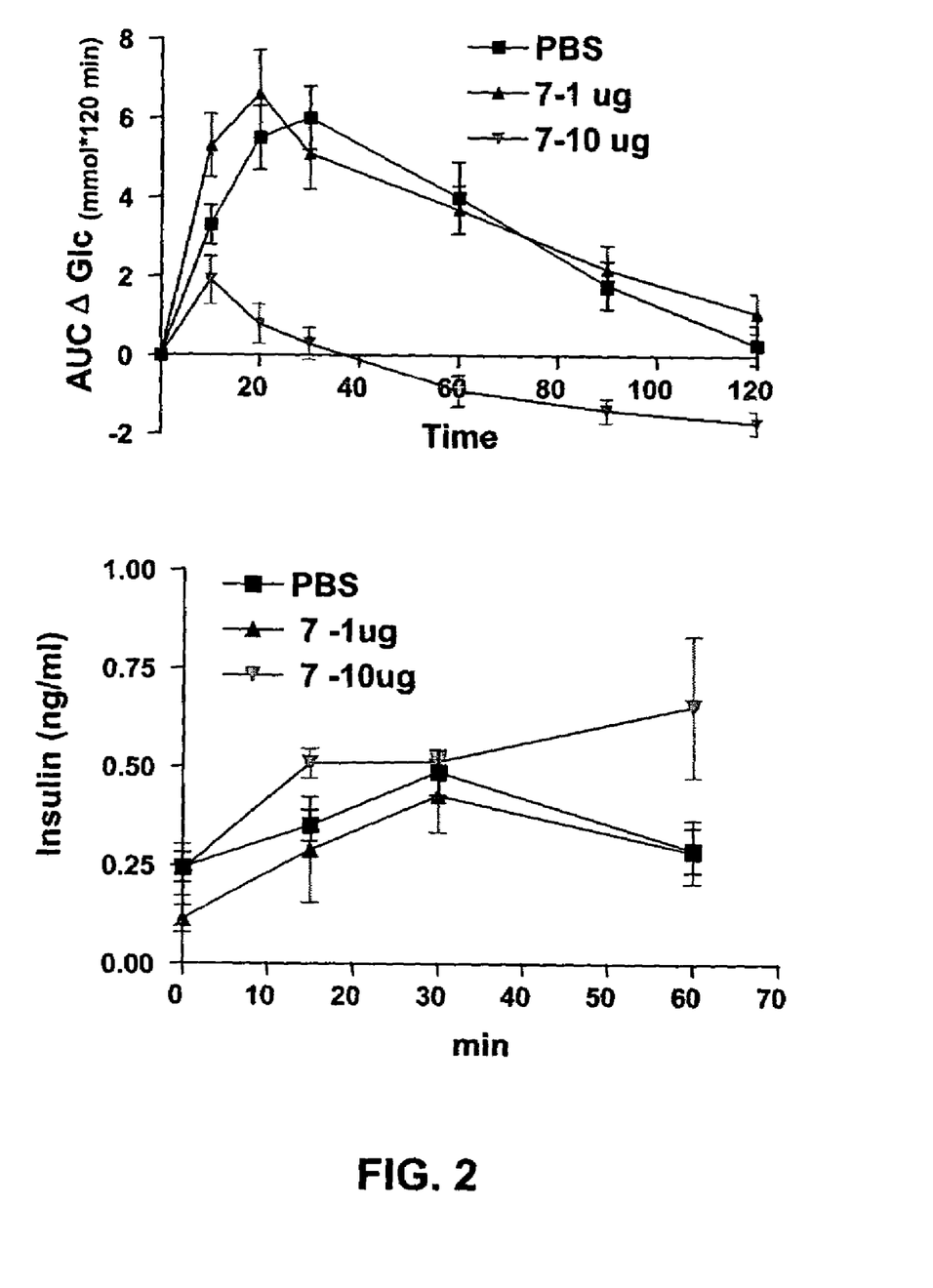
FIG. 2 illustrates glucose clearance and plasma insulin levels produced by ip injection of compound 7 (1 and 10 μg/mouse)

Dose-Effect of Compound 7 on Glucose and Insulin Levels in Normal CD-1 Female Mice An OGTT was done as described above. Plasma insulin levels were determined using a commercial RIA kit (Linco Research). The results are shown in FIG. 2. Compound 7 was administered ip and blood glucose (mmol/L) and plasma insulin levels (ng/ml) by RIA (Linco Research) were measured. It was found that there was no effect on glucose disposal using 1 μg doses. However, 10 μg of compound 7 significantly improved glucose clearance in CD-1 mice. Correspondingly, the plasma insulin levels were higher at 15 and 60 minutes following treatment with 10 μg of compound 7.

EXAMPLE 5

Effect of GLP-1 Analogues in the OGTT in Diabetic Mice (db/db)

Figure 3:
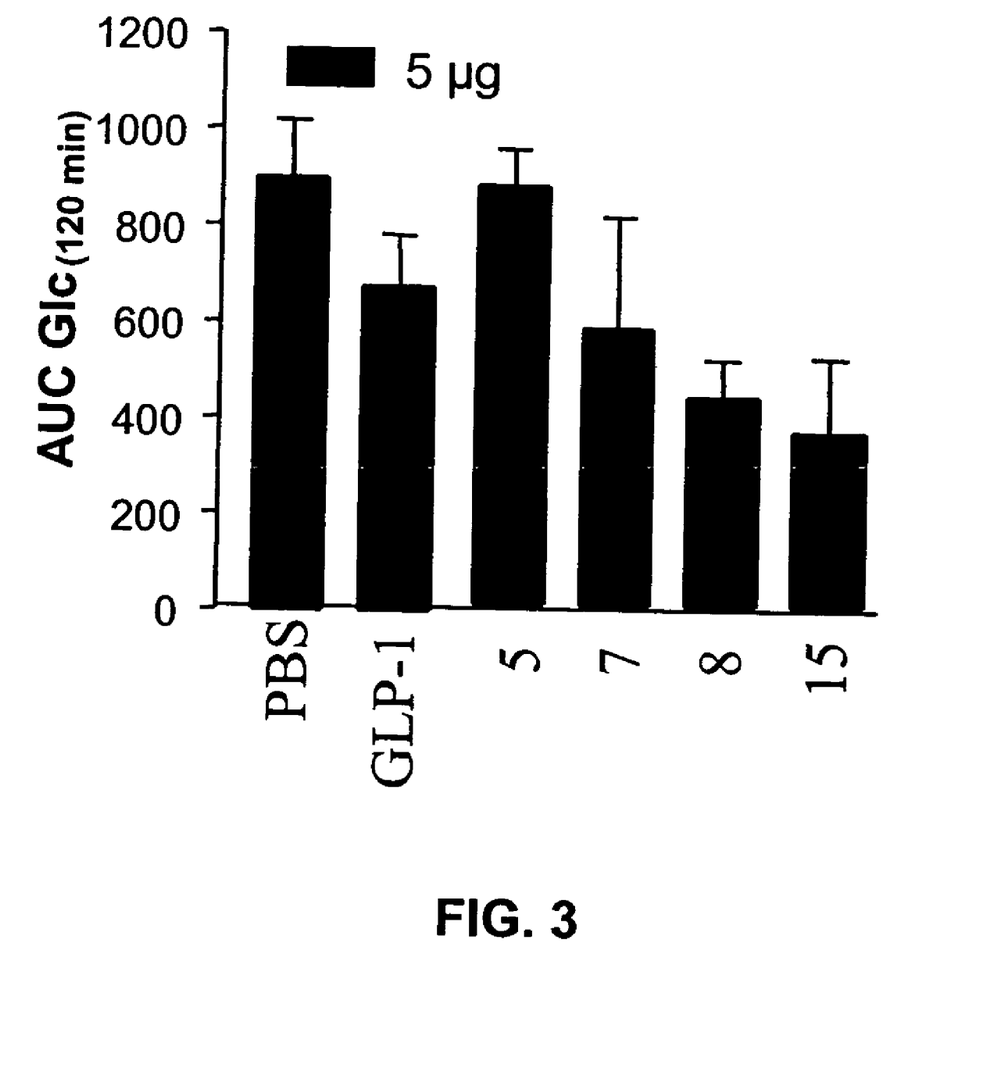
FIG. 3 illustrates glucose clearance in db/db mice (female; 8–10 wks; C57BLKS/J-M+/+Lepr$^{db}$; Jackson laboratories, Bar Harbor, Mich.) in response to GLP-1 analogues.

A genetic mutation at the leptin receptor locus renders this strain of mice diabetic, and has been used as a useful model for diabetes. An OGTT was conducted as described in Example 3. Peptides were injected intra-parentally (ip) at 5 μG/mouse doses. The results are shown in FIG. 3 (peptide administration, OGTT and glucose measurements were performed as described in the legend for FIG. 1). Three peptides, 7, 8 and 15 performed better than GLP-1 in accelerating glucose disposal in this model.

EXAMPLE 6

Figure 4:
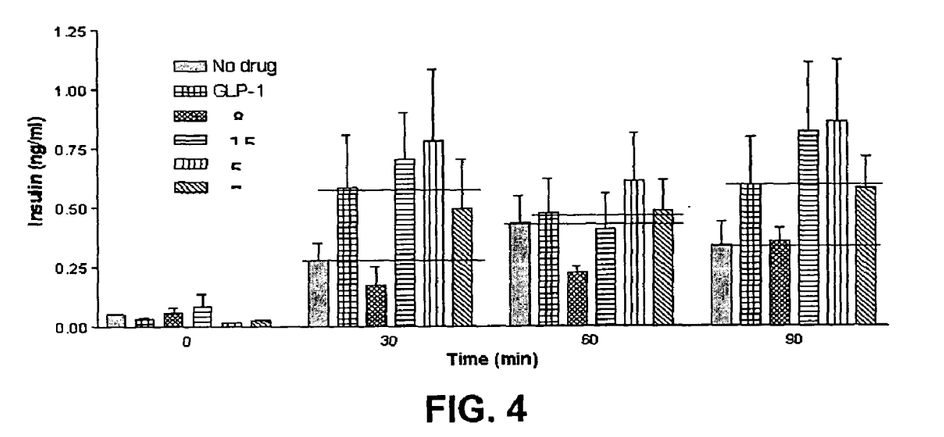
FIG. 4 illustrates plasma insulin levels using the Intraperitoneal Glucose Tolerance Test (IPGTT), in rats injected iv with GLP-1 analogues.
Figure 5:
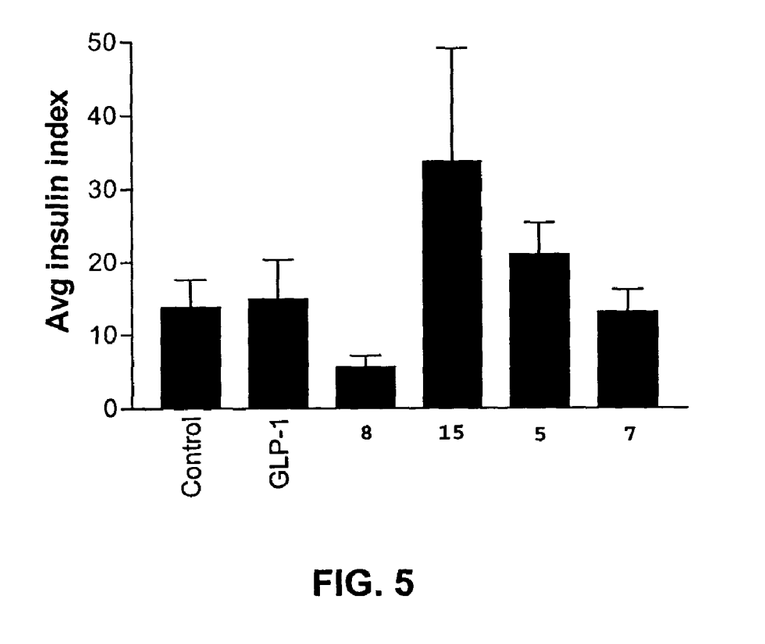
FIG. 5 illustrates the average insulinogenic index of GLP-1 analogues.

Effect of GLP-1 Analogues on Plasma Insulin Levels in the Intraperitoneal Glucose Tolerance Test (IPGTT) Using Sprague-Dawley rats Sprague-Dawley rats (300–350 g) were fasted overnight, and injected with 1 g/kg glucose (2 ml) (over 15–20 seconds), and blood glucose levels were determined at different times during a period of 3 hours using a portable glucometer. The drugs (10 μg/rat) were dissolved in saline and injected into the femoral vein 5 minutes before the injection of glucose. Thus 0 time represents blood glucose and insulin levels after drug administration but before glucose injection. Plasma insulin levels were determined using a radioimmunoassay kit (Linco). Glucose and insulin levels are shown in mmol/L and ng/ml respectively. The insulinogenic index was calculated as delta insulin (pM)/delta glucose (mM). The results are shown in FIG. 4. In all groups of rats, the basal insulin levels were not affected by GLP-1 analogues alone. Glucose injections produced rapid responses in plasma insulin levels and the values obtained at 0, 30, 60, 90 minutes following glucose administration are shown in the bar graph. Cross bars are shown to indicate the relative levels compared to saline (n=8) and GLP-1 (n=4) injections. Based on these results, 5 (n=4) and 15 (n=4) produced higher average insulin levels than GLP-1, whereas 7 (n=4) was similar to GLP-1 in response. The order of efficacy in these experiments was found to be 15=5>7=GLP-1>8=vehicle.

EXAMPLE 7

Fed C57BL/ks db/db Mice

Figure 6:
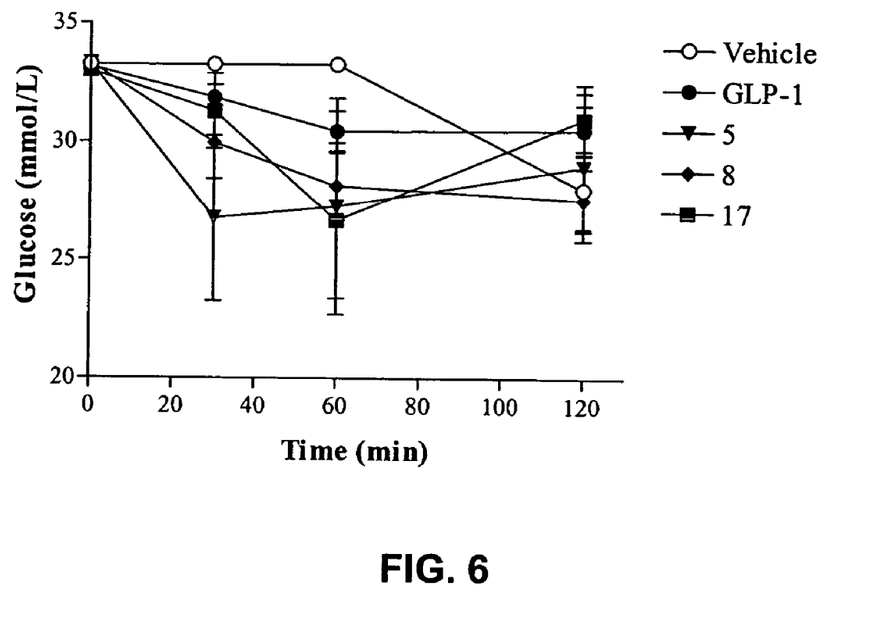
FIG. 6 illustrates glucose levels, following 30 minutes of feeding, in overnight fasted C57BL/ks db/db mice (Harlan) injected subcutaneously with GLP-1 and compounds 5, 8, and 17 (500 μg/kg; n=6)

C57BL/ks db/db mice were fasted overnight and then allowed free access to food for a period of 30 minutes. Immediately following feeding, sc injections of vehicle, GLP-1, 5, 8, or 17 (500 µg/kg) were given, and glucose levels measured for 2 hours in blood drawn from a tail cut. Blood glucose levels (mmol/L) were determined using an AccuCheck compact glucometer (Roche, Germany). The obtained data are presented in FIG. 6 as Mean±SEM.

EXAMPLE 8

Glucose Clamp in Sprague-Dawley Rats

Figure 7:
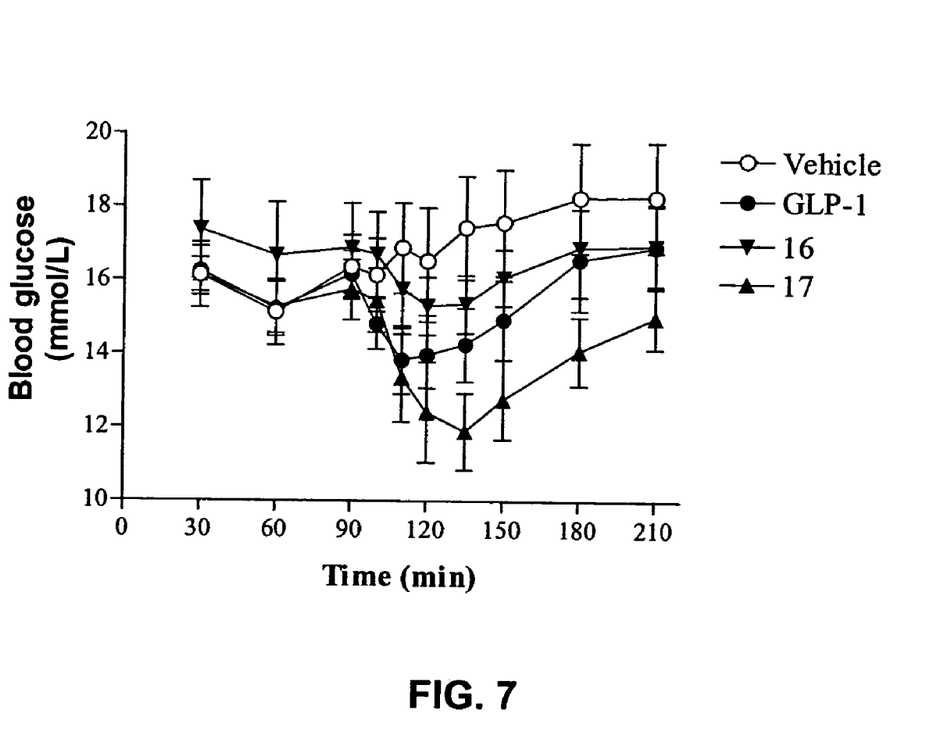
FIG. 7 illustrates the effect of GLP-1, 16, or 17 (300 μg/rkg subcutaneous; n=6) on glucose levels during a hyperglycemic clamp in Sprague-Dawley rats.

Rats were fasted overnight, anesthetized (isoflurane 2%) and catheterized to receive intravenous glucose at a rate and concentration such as to maintain a glycemia between 16 and 18 mmol/L blood glucose. After reaching a stable glucose level and stabilizing it for a period of 1 hour, subcutaneous injections of vehicle, GLP-1, 16, or 17 (300 pg/kg) were administered and glucose levels measured for an additional 2 hours. Blood samples were drawn from interdigital punctures and blood glucose levels (mmol/L) monitored by an AccuCheck compact glucometer (Roche, Germany). The obtained data are presented in FIG. 7.

EXAMPLE 9

DPPIV Resistance Assay

Figure 8:
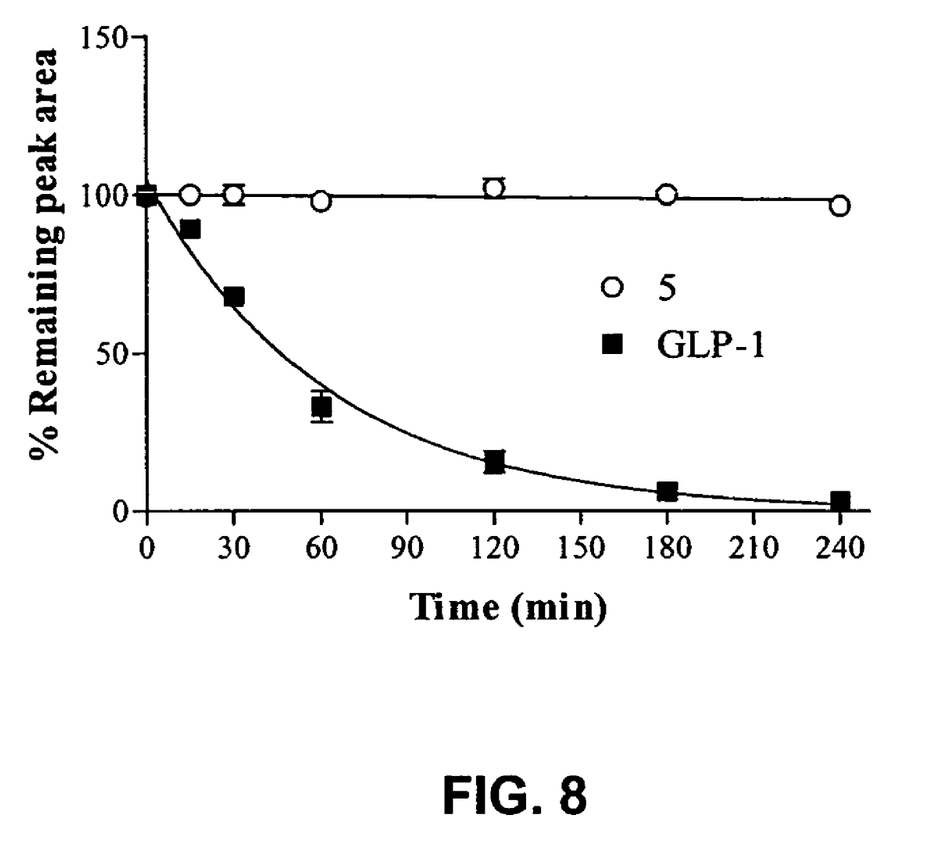
FIG. 8 illustrates a DPP IV degradation assay.

Aliquots (100 µg) of GLP-1 (7–37) or 5 were incubated at room temperature (22–24° C.) in duplicates with 50 mU of DPP IV (Sigma-Aldrich), in 20 mM Tris-HCL buffer, pH 8.0. The reaction mixture was sampled at different times and directly analysed by RP-HPLC using Vydac $C_{18}$ columns. The peak areas were determined by Chemstation rev. A.05.01 data analysis software (Agilent Technologies). The observed data are expressed as the % remaining area in comparison to the undigested controls and are shown in FIG. 8.

Although the present invention has been described hereinabove by way of preferred embodiments thereof, it can be modified without departing from the spirit and nature of the subject invention as defined in the appended claims.

REFERENCES

The following references, to the extent that they provide exemplary procedural or other details supplementary to those set forth herein, are specifically incorporated herein by reference.

U.S. Pat. No. 5,512,549
U.S. Pat. No. 5,545,618
Adelhorst et al., *J. Biol. Chem.*, 269(9):6275–6278, 1994.
Burcelin et al., *Metabolism*, 48(2):252–258, 1999.
D'Alessio et al., *Diabetes*, 46(Suppl 1):29A, 1997.
Deacon et al., *Diabetologia*, 41:271–278, 1998.
Doyle and Egan, *Recent Prog. Horm. Res.*, 56:377–399, 2001.
Doyle et al., *Endocrinol.*, 142(10):44624468, 2001.
Drucker, *Endocrinol.*, 142(2):521–527, 2001.
Dugas and Penney, In: *Bioorganic Chemistry*, Springer-Verlag, N.Y., 54–92, 1981.
EP 0 733,644
Gorrell et al., *Scand. J. Immunol.*, 54(3):249–264, 2001.
Gutniak et al., *New Engl. J. Med.*, 326:1316–1322, 1992.
Gutniak, *Intl. Diabet. Monitor*, 9(2):1–12, 1997.
Holst, *Gastroenterology*, 107:1848–1855, 1994.
Holst, *Trends Endocrinol. Metab.*, 10(6):229–235, 1999.
Holz et al., *J. Biol. Chem.*, 270:17749–17757, 1995.
Kieffer and Habener, *Endocrine*, 20(6):876–913, 1999.
Kreymann et al., *Lancet.*, 2(8571):1300–1304, 1987.
Merrifield, *Chem. Soc.*, 85:2149,1962.
Nauck et al., *Diabetologia*, 29:46–52, 1986.
Nauck et al., *Ibid*, 36:741–744, 1993.
Nauck, *Cur. Opin. Endocrinol. Diabet*, 4:291–299,1997.
PCT Appln. WO 91/11457
PCT Appln. WO 99/43707
Peptide synthesis protocols: Methods in molecular biology Vol. 35. Pennington and Dunn (Eds), Humana Press, 1994.
Perfetti and Merkel, *Eur. J. Endocrinol.*, 143:717–725, 2000.
Remington's Pharmaceutical Sciences, 15th ed., 33:624–652, Mack Publishing Company, Easton, Pa., 1980.
Scrocchi et al., *Nat. Med.*, 2:1254–1258, 1996.
Siegel et al., *Reg. Peptides*, 79:93–102, 1999.
Stewart and Young, In: Solid Phase Peptide Synthesis, 24–66, Freeman, San Francisco, 1969.
Suzuki et al., *Diabetes Res.*, 5(Supp. 1):S30, 1988.
Toft-Nielsen et al., *Diabetes Care*, 22:1137–1143. 1999.
Tolessa et al., *J. Clin. Invest.*, 102:764–774, 1998.
Wang et al., *J. Clin. Invest.*, 99:2883–2889, 1997.
Xiao et al., *Biochemistry*, 40:2860–2869, 2001.
Xu et al., *Diabetes*, 48:2270–2276, 1999.

The invention claimed is:

1. A GLP-1 peptide having the following formula, or a pharmaceutically acceptable salt thereof:

X-His-Ala-Glu-Gly-Thr-Phe-Thr-Ser-Asp-Val-Ser-
Ser-Tyr-Leu-Glu-Gly-Gln-Ala-Ala-Lys-Glu-Phe-
Ile-Ala-Trp-Leu-Val-Lys-Gly-Arg-Y (SEQ ID
NO.1)

wherein:
X is a rigidifying hydrophobic acyl moiety as obtained from the corresponding carboxylic acid of general structure I:

I wherein R1 is 2- or 3-lower alkoxy, 2- or 3-hydroxy, 2- or 3- amino, 2-N-phenylamino, 2,6-dihalo or 2,3,4,5,6-pentahalo and n=0 or 1, and Y is selected from the group consisting of OH, $NH_2$ and Gly-OH.

2. A composition comprising a therapeutically effective amount of a peptide of claim 1, or a pharmaceutically acceptable salt thereof, in association With at least one constituent selected from the group consisting of pharmaceutically acceptable carrier, diluent, and excipient.

3. The composition of claim 2, wherein said therapeutically effective amount is comprised between about 1 mcg and about 10 mg.

4. A method for treating or preventing a disease or condition associated with a disorder of glucose metabolism comprising administering to a subject in need thereof a therapeutically effective amount of the peptide of claim 1.

5. The method of claim 4, wherein said disease or condition associated with a disorder of glucose metabolism is selected from diabetes mellitus of Type I or Type II and insulin resistance.

6. The method of claim 5, wherein said condition is diabetes mellitus of Type I or Type II.

7. The method of claim 5, wherein said condition is insulin resistance.

8. The method of claim 4, wherein said disease or condition is a weight disorder or associated condition.

9. The method of claim 8, wherein said weight disorder or associated condition is selected from at least one of lowering weight, increasing satiety, post-prandially increasing plasma insulin levels, reducing blood glucose levels, and increasing pancreatic beta cell mass in said subject.

10. The method of claim 9, wherein said lowering weight is from about 1 to about 10 kg.

11. The method of claim 9, wherein said increasing satiety is of the order of about 10%.

12. The method of claim 9, wherein said post-prandially increasing plasma insulin levels is of the order of about 10%.

13. The method of claim 9, wherein said reducing blood glucose levels is of the order of about 10%.

14. The method of claim 9, wherein said increasing pancreatic beta cell mass is of at least about 10%.

15. The method of claim 4, wherein said peptide, or pharmaceutically acceptable salt thereof, is administered to said subject through an administration route selected from the group consisting of subcutaneous, intravenous, transdermal, oral, buccal and intranasal.

16. The method of claim 4, wherein said subject is a human.

17. A composition comprising a prophylactically effective amount of a peptide of claim 1, or a pharmaceutically acceptable salt thereof, in association with at least one constituent selected from the group consisting of pharmaceutically acceptable carrier, diluent and excipient.

18. The peptide of claim 1 wherein:
R1=2-hydroxy and n=0,
R1=2-ethoxy and n=0,
R1=3-methoxy and n=1,
R1=3-amino and n=1,
R1=2-N-phenylamino and n=0,
R1=2,6-difluoro and n=1, or
R1=2,3,4,5,6-pentafluoro and n=1.

19. The peptide of claim 1 wherein the corresponding carboxylic acid is selected from the group consisting of and 20. The peptide of claim 1 wherein the corresponding carboxylic acid is and Y is NH$_2$.

21. The peptide of claim 1 wherein the corresponding carboxylic acid is and Y is Gly-OH.

22. The peptide of claim 1 wherein the corresponding carboxylic acid is and Y is Gly-OH.

23. The peptide of claim 1 wherein the corresponding carboxylic acid is and Y is NH$_2$.

* * * * *

UNITED STATES PATENT AND TRADEMARK OFFICE
CERTIFICATE OF CORRECTION

| | | |
|---|---|---|
| PATENT NO. | : 7,067,488 B2 | Page 1 of 1 |
| APPLICATION NO. | : 10/671340 | |
| DATED | : June 27, 2006 | |
| INVENTOR(S) | : Gravel et al. | |

It is certified that error appears in the above-identified patent and that said Letters Patent is hereby corrected as shown below:

In claim 1, column 19, line 40, delete "With at" and insert --with at-- therefor.

Signed and Sealed this

Seventh Day of November, 2006

JON W. DUDAS
*Director of the United States Patent and Trademark Office*